(12) United States Patent
Natsume et al.

(10) Patent No.: US 7,700,362 B2
(45) Date of Patent: Apr. 20, 2010

(54) METHOD FOR SCREENING THERAPEUTIC AGENTS FOR DISUSE MUSCULAR ATROPHY USING INTERACTION BETWEEN SELECTED PROTEINS AND A POLYUBIQUITIN CHAIN

(75) Inventors: Tohru Natsume, Koto-ku (JP); Ken Watanabe, Obu (JP)

(73) Assignees: National Institute of Advanced Industrial Science and Technology, Tokyo (JP); National Center for Geriatrics and Gerontology, Aichi (JP)

( * ) Notice: Subject to any disclaimer, the term of this patent is extended or adjusted under 35 U.S.C. 154(b) by 348 days.

(21) Appl. No.: 10/581,969

(22) PCT Filed: Dec. 7, 2004

(86) PCT No.: PCT/JP2004/018179

§ 371 (c)(1),
(2), (4) Date: Apr. 30, 2007

(87) PCT Pub. No.: WO2005/056590

PCT Pub. Date: Jun. 23, 2005

(65) Prior Publication Data

US 2008/0227694 A1     Sep. 18, 2008

(30) Foreign Application Priority Data

Dec. 8, 2003   (JP)   ............................ 2003-408744

(51) Int. Cl.
*H01L 21/20*   (2006.01)
(52) U.S. Cl. ........................................................ 436/86
(58) Field of Classification Search ................... 436/86
See application file for complete search history.

(56) References Cited

U.S. PATENT DOCUMENTS 5,817,494 A   10/1998   Bandman et al.

FOREIGN PATENT DOCUMENTS

WO     98/53079 A1    11/1998
WO     00/77255       * 12/2000

OTHER PUBLICATIONS

Keiji Tanaka, "Magic of ubiquitin that sends out new troops", *Experimental Medicine*, Feb. 2003, vol. 21, No. 3, pp. 330-339, Partial.
Marcelo D. Gomes et al., "Atrogin-1, a muscle-specific F-box protein highly expressed during muscle atrophy", *Proc. Natl. Acad. Sci.*, Dec. 4, 2001, vol. 98, No. 25, pp. 14440-14445.
Sue C. Bodine et al., "Identification of Ubiquitin Ligases Required for Skeletal Muscle Atrophy", *Science*, Nov. 23, 2001, vol. 294, pp. 1704-1708.
D.A. Scott et al., "Identification and mutation analysis of a cochlear-expressed, zinc finger protein gene at the DFNB7/11 and *dn* hearing-loss-loci on human chromosome 9q and mouse chromosome 19", *Gene*, 215 (1998), pp. 461-469.
Wei Duan et al., "Cloning and characterization of AWP1, a novel protein that associates with serine/threonine kinase PRK1 in vivo", *Gene*, 256 (2000), pp. 113-121.
Chen, Li and Madura, Kiran; "Rad23 Promotes the Targeting of Proteolytic Substrates to the Proteasome", *Modecular and Cellular Biology*, Jul. 2002, vol. 22, No. 13, pp. 4902-4913.
Hishiya, Akinori; Iemura, Shun-Ichiro; Natsume, Tohru; Takayama, Shinichi; Ikeda, Kyoji; and Watanabe, Ken; "A novel ubiquitin-binding protein ZNF216 functioning in muscle atrophy", *The EMBO Journal*, vol. 25, No. 3, 2006, pp. 554-564.

* cited by examiner

*Primary Examiner*—Maryam Monshipouri
(74) *Attorney, Agent, or Firm*—Roberts Mlotkowski Safran & Cole, P.C.; Thomas W. Cole

(57) ABSTRACT

A method for screening therapeutic agents for disuse muscular atrophy is provided that includes the steps of interacting a selected protein with a polyubiquitin chain in the presence of a candidate therapeutic agent, and determining the effect of the candidate on the binding strength between the protein and the polyubiquitin chain. The effect may be observed by color development on a substrate when the steps are carried out by way of an enzyme-linked immunosorbent assay, or by direct observation via NMR spectroscopy, X-ray crystal analysis, electron microscopy or surface plasmon resonance.

5 Claims, No Drawings

SEQUENCE LISTING

```
<160> NUMBER OF SEQ ID NOS: 5

<210> SEQ ID NO 1
<211> LENGTH: 213
<212> TYPE: PRT
<213> ORGANISM: Homo sapiens
<220> FEATURE:
<223> OTHER INFORMATION: ZNF216(Zub 1)

<400> SEQUENCE: 1

Met Ala Gln Glu Thr Asn Gln Thr Pro Gly Pro Met Leu Cys Ser
1               5                   10                  15

Thr Gly Cys Gly Phe Tyr Gly Asn Pro Arg Thr Asn Gly Met Cys
                20                  25                  30

Ser Val Cys Tyr Lys Glu His Leu Gln Arg Gln Gln Asn Ser Gly
                35                  40                  45

Arg Met Ser Pro Met Gly Thr Ala Ser Gly Ser Asn Ser Pro Thr
                50                  55                  60

Ser Asp Ser Ala Ser Val Gln Arg Ala Asp Thr Ser Leu Asn Asn
                65                  70                  75

Cys Glu Gly Ala Ala Gly Ser Thr Ser Glu Lys Ser Arg Asn Val
                80                  85                  90

Pro Val Ala Ala Leu Pro Val Thr Gln Gln Met Thr Glu Met Ser
                95                  100                 105

Ile Ser Arg Glu Asp Lys Ile Thr Thr Pro Lys Thr Glu Val Ser
                110                 115                 120

Glu Pro Val Val Thr Gln Pro Ser Pro Ser Val Ser Gln Pro Ser
                125                 130                 135

Thr Ser Gln Ser Glu Glu Lys Ala Pro Glu Leu Pro Lys Pro Lys
                140                 145                 150

Lys Asn Arg Cys Phe Met Cys Arg Lys Lys Val Gly Leu Thr Gly
                155                 160                 165

Phe Asp Cys Arg Cys Gly Asn Leu Phe Cys Gly Leu His Arg Tyr
                170                 175                 180

Ser Asp Lys His Asn Cys Pro Tyr Asp Tyr Lys Ala Glu Ala Ala
                185                 190                 195

Ala Lys Ile Arg Lys Glu Asn Pro Val Val Ala Glu Lys Ile
                200                 205                 210

Gln Arg Ile

<210> SEQ ID NO 2
<211> LENGTH: 208
<212> TYPE: PRT
```

<213> ORGANISM: Homo sapiens
<220> FEATURE:
<223> OTHER INFORMATION: AWP1(Zub 2)

<400> SEQUENCE: 2

```
Met Ala Gln Glu Thr Asn His Ser Gln Val Pro Met Leu Cys Ser
 1               5                  10                  15

Thr Gly Cys Gly Phe Tyr Gly Asn Pro Arg Thr Asn Gly Met Cys
                20                  25                  30

Ser Val Cys Tyr Lys Glu His Leu Gln Arg Gln Asn Ser Ser Asn
                35                  40                  45

Gly Arg Ile Ser Pro Pro Ala Thr Ser Val Ser Ser Leu Ser Glu
                50                  55                  60

Ser Leu Pro Val Gln Cys Thr Asp Gly Ser Val Pro Glu Ala Gln
                65                  70                  75

Ser Ala Leu Asp Ser Thr Ser Ser Ser Met Gln Pro Ser Pro Val
                80                  85                  90

Ser Asn Gln Ser Leu Leu Ser Glu Ser Val Ala Ser Ser Gln Leu
                95                 100                 105

Asp Ser Thr Ser Val Asp Lys Ala Val Pro Glu Thr Glu Asp Val
               110                 115                 120

Gln Ala Ser Val Ser Asp Thr Ala Gln Gln Pro Ser Glu Glu Gln
               125                 130                 135

Ser Lys Ser Leu Glu Lys Pro Lys Gln Lys Lys Asn Arg Cys Phe
               140                 145                 150

Met Cys Arg Lys Lys Val Gly Leu Thr Gly Phe Glu Cys Arg Cys
               155                 160                 165

Gly Asn Val Tyr Cys Gly Val His Arg Tyr Ser Asp Val His Asn
               170                 175                 180

Cys Ser Tyr Asn Tyr Lys Ala Asp Ala Ala Glu Lys Ile Arg Lys
               185                 190                 195

Glu Asn Pro Val Val Val Gly Glu Lys Ile Gln Lys Ile
               200                 205
```

<210> SEQ ID NO 3
<211> LENGTH: 642
<212> TYPE: DNA
<213> ORGANISM: Homo sapiens
<220> FEATURE:
<223> OTHER INFORMATION: ZNF216

<400> SEQUENCE: 3

| | | | | | |
|---|---|---|---|---|---|
| atggctcagg | agactaacca | gaccccgggg | cccatgctgt | gtagcacagg | 50 |
| atgtggcttt | tatggaaatc | ctaggacaaa | tggaatgtgt | tcagttttgct | 100 |
| acaaagaaca | tcttcagagg | cagcaaaata | gtggcagaat | gagcccaatg | 150 |
| gggacagcta | gtggttccaa | cagtcctacc | tcagattctg | catctgtaca | 200 |
| gagagcagac | actagcttaa | caactgtga | aggtgctgct | ggcagcacat | 250 |
| ctgaaaaatc | aagaaatgtg | cctgtggctg | ccttgcctgt | aactcagcaa | 300 |
| atgacagaaa | tgagcatttc | aagagaggac | aaaataacta | ccccgaaaac | 350 |
| agaggtgtca | gagccagttg | tcactcagcc | cagtccatca | gtttctcagc | 400 |
| ccagtacttc | tcagagtgaa | gaaaaagctc | ctgaattgcc | caaaccaaag | 450 |
| aaaaacagat | gtttcatgtg | cagaaagaaa | gttggtctta | cagggtttga | 500 |
| ctgccgatgt | ggaaatttgt | tttgtggact | tcaccgttac | tctgacaagc | 550 |

```
acaactgtcc gtatgattac aaagcagaag ctgcagcaaa aatcagaaaa              600
gagaatccag ttgttgtggc tgaaaaaatt cagagaatat aa                     642

<210> SEQ ID NO 4
<211> LENGTH: 627
<212> TYPE: DNA
<213> ORGANISM: Homo sapiens
<220> FEATURE:
<223> OTHER INFORMATION: AWP1

<400> SEQUENCE: 4
atggctcaag aaactaatca cagccaagtg cctatgcttt gttccactgg               50
ctgtggattt tatggaaacc ctcgtacaaa tggcatgtgt tcagtatgct              100
ataaagaaca tcttcaaaga cagaatagta gtaatggtag aataagccca              150
cctgcaacct ctgtcagtag tctgtctgaa tctttaccag ttcaatgcac              200
agatggcagt gtgccagaag cccagtcagc attagactct acatcttcat              250
ctatgcagcc cagccctgta tcaaatcagt cacttttatc agaatctgta              300
gcatcttctc aattggacag tacatctgtg gacaaagcag tacctgaaac              350
agaagatgtg caggcttcag tatcagacac agcacagcag ccatctgaag              400
agcaaagcaa gtctcttgaa aaaccgaaac aaaaaaagaa tcgctgtttc              450
atgtgcagga agaaagtggg acttactggg tttgaatgcc ggtgtggaaa              500
tgtttactgt ggtgtacacc gttactcaga tgtacacaat tgctcttaca              550
attacaaagc cgatgctgct gagaaaatca gaaaagaaaa tccagtagtt              600
gttggtgaaa agatccaaaa gatttga                                      627

<210> SEQ ID NO 5
<211> LENGTH: 70
<212> TYPE: RNA
<213> ORGANISM: Homo sapiens
<220> FEATURE:
<223> OTHER INFORMATION: siRNA of AWP1

<400> SEQUENCE: 5
ggaucccaug gcauguguuc aguauguuca agagacauac ugaacacaug               50
ccauuuuuuu ggaagucgac                                                70
```

US 7,700,362 B2

METHOD FOR SCREENING THERAPEUTIC AGENTS FOR DISUSE MUSCULAR ATROPHY USING INTERACTION BETWEEN SELECTED PROTEINS AND A POLYUBIQUITIN CHAIN

This application is a 371 of PCT/JP04/18179 filed Dec. 7, 2004, which claims priority to Japanese application No. Japan 2003-408744 filed Dec. 8, 2003.

TECHNICAL FIELD

The present invention relates to a novel interaction between proteins, and further relates to a therapeutic agent for disuse muscular atrophy, and a method for screening the therapeutic agent for disuse muscular atrophy, a marker for diagnosing the disease and a method for evaluating the risk of onset, based on the novel interaction between the proteins.

BACKGROUND ART

Analysis of DNA base sequences in the human genome (entire gene information) has been nearly completed and future research tasks have shifted to elucidating functions of the genes encoded by DNA. Much of gene information encoded by the DNA relates to proteins, and the research to elucidate the functions of the genes by demonstrating structures, functions and roles of the proteins have been performed in various research institutions.

Many proteins are expressed based on the genetic information in vivo, and vital activity is maintained by interaction of those proteins. For example, in a citric acid cycle which is a typical metabolic pathway in cells, pyruvic acid is decomposed by interactions of a plurality of enzymes (proteins) to supply energy for producing ATP.

Many of the diseases caused in vivo are believed to occur by producing abnormalities in the interaction between the proteins in the cells. For example, in the case of genetic diseases, the normal protein is not expressed, and thus, the necessary interaction between the proteins is absent or the abnormality occurs in the interaction between the proteins to cause a metabolic abnormality, and they result in generating the disease.

Therefore, concerning various proteins expressed in vivo, it is important to elucidate a reaction pathway in the cells or to reveal the function and the role of the protein in order to reveal the interaction between the proteins. By revealing the interaction between the proteins, it is possible to provide the information effective for elucidating onset mechanisms of various diseases or developing the therapeutic agent.

Here, four proteins, i.e., proteasome, ubiquitin, ZNF216 and AWP1 which are associated with the present invention will be described.

Proteasome is a macromolecular protease (proteolytic enzyme) localized in nuclei and cytoplasm and a protein with a molecular weight of 700,000 to 800,000 composed of 28 subunits. "26S Proteasome" obtained by binding PA70 (activation factor) to both ends of proteasome has the function to decompose the protein depending on ATP, and plays a main role in a ubiquitin/proteasome proteolytic system. 26S Proteasome selectively decomposes the protein polyubiquitinated (modified with a polyubiquitin chain) (Non-patent Document 1).

Proteasome is also involved in the occurrence mechanism of the disuse muscular atrophy (Non-patent Documents 2 and 3). The disuse muscular atrophy refers to reduced muscular size and lowered muscular force when a bedridden state continues and the state of not using muscles persists. It is thought that muscular size is reduced to cause the disease when the state of not using muscles persists because the proteins such as myosin which compose muscles are decomposed in the ubiquitin/proteasome proteolytic system.

Ubiquitin is a protein composed of 76 amino acids which is universally present in eukaryotic cells, and has the role to label the protein to be decomposed (target protein) in the ubiquitin/proteasome proteolytic system. In the ubiquitin/proteasome proteolytic system, the polyubiquitin chain plays the role to label the target protein. The polyubiquitin chain is formed by binding a large number of ubiquitin in a branched shape, and is bound to a particular site of the target protein. When the polyubiquitin chain is bound to the target protein, 26S proteasome recognizes the target protein and decomposes the target protein (see Non-patent document 1).

ZNF216 is a protein whose gene was identified as a zinc finger protein by D. A. Scot et al. in 1998 (Non-patent Document 4). AWP1 is a novel protein isolated by W. Duan et al. in 2000 (Non-patent Document 5). Specific functions and roles in vivo in both proteins are still unknown.

Non-patent Document 1: "Jikken Igaku" Vol. 21, No. 3, pp 330-332, February, 2003, Yodosha.

Non-patent Document 2: Gomes et al "Atrogin-1, a muscle-specific F-box protein highly expressed during muscle atrophy", Proc. Natl. Acad. Sci. USA, 2000, Vol. 98, No. 25, pp 14440-14445

Non-patent Document 3: Bodine et al "Identification of ubiquitin ligases required for skeletal muscle atrophy", Science, 2001, Vol. 294, pp 1704-1708

Non-patent Document 4: D. A. Ccott et al "Identification and mutation analysis of a cochlear-expressed, zinc finger protein gene at the DFNB7/11 and dn hearing-loss-loci on human chromosome 9q and mouse chromosome 19", AN INTERNATIONAL JOURNAL ON GENES AND GENOMES, Elsevier Science B.V., 1998, p 461-469

Non-patent Document 5: W. Duan et al "Cloning and characterization of AWP1, a novel protein that associates with serine/threonine kinase PRK1 in vivo", AN INTERNATIONAL JOURNAL ON GENES, GENOMES AND EVOLUTION, Elsevier Science B.V., 2000, p 113-121.

SUMMARY OF THE INVENTION

It remains unknown what protein many of the proteins expressed in vivo interact with or what function and role many of the proteins expressed in vivo have. Thus, the present invention provides a novel interaction between the proteins by exhaustively analyzing the interactions between the proteins. The present invention also provides a therapeutic agent for a particular disease by finding the interaction between the protein with an unknown function and the protein known to be involved in the occurrence of the particular disease. Furthermore, the present invention provides a method for screening for the above particular disease, a marker for diagnosis and a method for evaluating the risk of onset, based on this novel interaction, and in particular a method for screening therapeutic agents for treating disuse muscular atrophy.

DETAILED DESCRIPTION OF THE PREFERRED EMBODIMENTS

At this time, it has been newly found by the exhaustive analysis of the interaction between the proteins that proteasome which plays the main role in the proteolytic system interacts with ZNF216 (protein composed of SEQ ID No. 1) or AWP1 (protein composed of SEQ ID No. 2) whose functions in vivo are unknown. That is, ZNF216 or AWP1 has the nature to interact with proteasome, and proteasome has the nature to interact with ZNF216 or AWP1.

As described above, it has been known that the proteasome is involved in the occurrence mechanism of the disuse muscular atrophy. When a certain individual becomes bedridden, etc., in order to respond to the change in a life environment of the individual, it appears that various intracellular responses are caused in the respective cells of the individual. The intracellular responses are continuously transmitted by the interaction between the proteins, and finally, a proteolytic response in the protein which composes muscle occurs by the interaction with proteasome. Therefore, when the certain individual becomes bedridden, if a binding property of one interaction between the proteins is changed among many interactions between the proteins caused by the intracellular responses, it is possible to prevent muscular atrophy (decomposition of protein which composes muscle by proteasome).

Thus, the present invention provides a therapeutic agent for the disuse muscular atrophy, which inhibits the expression of ZNF216 or AWP1 having the nature to interact with proteasome. Since signal transduction by the interaction between ZNF216 or AWP1 and the proteasome is inhibited by inhibiting the expression of ZNF216 or AWP1, the decomposition of the protein which composes muscle by the proteasome is inhibited. Therefore, muscle is not reduced, and it is possible to prevent or treat the disuse muscular atrophy.

As a means for inhibiting the expression of ZNF216 or AWP1, RNA interference can be applied. The RNA interference refers to a phenomenon that double strand RNA decomposes mRNA specific for its sequence and consequently the expression of a corresponding gene is inhibited, and can also be practically applied to mammals by the use of short RNA (siRNA, short interfering RNA).

The double strand RNA according to the present invention has the sequence corresponding to a part (18 to 24 bases) of a DNA sequence (SEQ ID No. 3) encoding ZNF216 or a DNA sequence (SEQ ID No. 4) encoding AWP1. It is believed that this double strand RNA can inhibit the expression of ZNF216 or AWP1 to some extent even when it corresponds to any part of the target sequence (SEQ ID No. 3 or SEQ ID No. 4) as long as it is short (18 to 24 bases). However, it is more suitable that the double strand RNA does not contain a TTTT or AAAA sequence and the sequence predicted that a secondary structure of the RNA is opened is selected because the expression can be effectively inhibited.

Additionally, in order not to cause the interaction between ZNF216 or AWP1 and the proteasome, a therapeutic agent for the disuse muscular atrophy, which inhibits or suppresses the function of ZNF216 or AWP1 itself may be used. By inhibiting or suppressing the interaction itself between ZNF216 or AWP1 and the proteasome, it is also possible to prevent or treat the muscular atrophy.

At this time, it has also been found that the polyubiquitin chain which plays the role to label in the proteolytic system interacts with ZNF216 or AWP1 whose function in vivo is unknown. That is, ZNF216 or AWP1 has the nature to interact with the polyubiquitin chain, and the polyubiquitin chain has the nature to interact with ZNF216 or AWP1.

In the case of the disuse muscular atrophy, it is thought that the proteasome decomposes the muscle-composing protein to which the polyubiquitin chain is bound. The signal transduction in the polyubiquitin chain occurs by the interaction with ZNF216 or AWP1, and the polyubiquitin chain is bound to the muscle-composing protein. Thus, when the interaction between the polyubiquitin chain and ZNF216 or AWP1 is inhibited, the signal transduction is inhibited and the binding to the muscle-composing protein is inhibited. It is also thought that when the interaction between the polyubiquitin chain and ZNF216 or AWP1 is inhibited, the signal transduction is also inhibited and the interaction between the polyubiquitin chain and the proteasome is inhibited. Also in this case, the decomposition of the muscle-composing protein by proteasome is inhibited.

Thus, as with the above, the present invention provides a therapeutic agent for the disuse muscular atrophy, which inhibits the expression of ZNF216 or AWP1 having the nature to interact with the polyubiquitin chain. In order not to produce the signal transduction by the interaction between ZNF216 or AWP1 and the polyubiquitin chain, a therapeutic agent which directly inhibits or suppresses the function of ZNF216 or AWP1 itself may be used. By inhibiting or suppressing the interaction itself between ZNF216 or AWP1 and the polyubiquitin chain, it is also possible to prevent or treat the muscular atrophy.

Subsequently, in the present invention, in order to produce the therapeutic agent for the disuse muscular atrophy, the interaction between the proteasome and ZNF216 or AWP1 can be directly or indirectly used.

For example, in a process of steps for producing the therapeutic agent for the disuse muscular atrophy, it is possible to select an objective substance using a screening method utilizing the above interaction and utilize this substance for producing the therapeutic agent for the disuse muscular atrophy. Alternatively, when it is examined in quality whether the substance, which becomes a candidate of the therapeutic agent, correctly has an activity or not, the above interaction can be utilized. Additionally, this interaction can be utilized as the marker for disease diagnosis of the disuse muscular atrophy, and can be practically applied to the means for evaluating the risk of onset.

Thus, the present invention provides a method for screening the therapeutic agent for the disuse muscular atrophy, which utilizes the interaction between the proteasome and ZNF216 or AWP1. By the method for screening according to the present invention, it is possible to perform the screening of compounds capable of changing (inhibiting or augmenting) the binding property of the interaction between the proteins to be subjected. Such a compound can become the candidate of the therapeutic agent or the preventive agent for disease (illness) with which the interaction between the proteins to be subjected is associated.

Such a screening includes a technique in which the candidate compound is added at appropriate concentrations to a reaction condition for detecting the above interaction and an effect on the interaction is examined. In this technique, screening is possible as the same technique as the conventional enzyme-linked immunosorbent assay (ELISA). The proteasome, ZNF216 or AWP1 is immobilized onto a 96 well plate, a molecule subjected to the screening is added thereto, further ZNF216 or AWP1 (proteasome in the case of immobilizing ZNF216 or AWP1), a labeled antibody and a substrate are sequentially reacted, and the change in binding between the proteasome and ZNF216 or AWP1 is examined in the presence of the substance subjected to the screening. The strong color development in the substrate corresponds to the strong binding.

The screening of drugs is also possible by direct observation of one molecule using NMR spectroscopy, X-ray crystal analysis or electron microscopy, etc. Efficient screening is also possible using surface plasmon resonance sensor (SPR).

Either proteasome or ZNF216 is immobilized on a sensor chip of SPR, and the solution of ZNF216 or AWP1 (proteasome in the case of immobilizing ZNF216 or AWP1) to which the molecule subjected to the screening has been added is sent to the sensor chip. The binding of both is observed in real-time as a binding curve by the surface plasmon resonance. When the binding of both is strengthened, the binding curve becomes large whereas when it is weakened, the curve is attenuated or disappears.

The present invention also provides the marker for prevention or diagnosis of the disuse muscular atrophy, composed of ZNF216 or AWP1 or the gene encoding the protein.

Based on quite new findings obtained by results of an extensive study by the present inventors that ZNF216 or AWP1 interacts with the proteasome which is obviously involved in the disuse muscular atrophy, it has been found that ZNF216 or AWP1 or the gene encoding this protein is involved in the onset of the disuse muscular atrophy. From this, it can assist the diagnosis of the disuse muscular atrophy that the expression of ZNF216 or AWP1 or the mutation (single nucleotide polymorphism) of the gene encoding this protein are examined. That is, the gene encoding ZNF216 or AWP1 becomes the marker for diagnosis of the disuse muscular atrophy.

Furthermore, the present invention provides a method for evaluating the risk of onset of the disuse muscular atrophy, which uses ZNF216 or AWP1 or the gene encoding this protein.

The risk of onset of the disuse muscular atrophy when an individual would become bedridden in the future can be evaluated by examining the expression of ZNF216 or AWP1 found to be involved in the disuse muscular atrophy via proteasome and examining the mutation or the single nucleotide polymorphism in the gene encoding this protein.

Subsequently, as with the case of utilizing the above-described interaction between the proteasome and ZNF216 or AWP1, in the present invention, for producing the therapeutic agent for the disuse muscular atrophy, it is also possible to directly or indirectly use the interaction between the polyubiquitin chain and ZNF216 or AWP1.

For example, in a process of steps for producing the therapeutic agent for the disuse muscular atrophy, it is possible to select an objective substance using a screening method utilizing the above interaction and utilizing this substance for producing the therapeutic agent for the disuse muscular atrophy. Alternatively, when it is examined in quality whether the substance, which becomes the candidate of the therapeutic agent correctly, has the activity or not, the above interaction can be utilized. Additionally, this interaction can be utilized as the marker for disease diagnosis of the disuse muscular atrophy, and can be practically applied to the means for evaluating the risk of onset.

Thus, the present invention also provides a method for screening the therapeutic agent for the disuse muscular atrophy, which utilizes the interaction between the polyubiquitin chain and ZNF216 or AWP1. As with the case of utilizing the above-described interaction between the proteasome and ZNF216 or AWP1, by the method for screening according to the present invention, it is possible to perform the screening of compounds capable of changing (inhibiting or augmenting) the binding property of the interaction between the proteins to be subjected. Such a compound can become the candidate of the therapeutic agent or the preventive agent for a disease (illness) with which the interaction between the proteins to be subjected is associated.

The present invention also provides the marker for prevention or diagnosis of the disuse muscular atrophy, composed of ZNF216 or AWP1 or the gene encoding the protein.

That is, based on quite new findings obtained by results of an extensive study by the present inventors that ZNF216 or AWP1 interacts with the polyubiquitin chain which is obviously involved in the disuse muscular atrophy, it has been found that ZNF216 or AWP1 or the gene encoding this protein is involved in the onset of the disuse muscular atrophy. From this, as with the case of utilizing the above-described interaction between the proteasome and ZNF216 or AWP1, it can assist the diagnosis of the disuse muscular atrophy that the expression of ZNF216 or AWP1 or the mutation (single nucleotide polymorphism) of the gene encoding this protein are examined. That is, the gene encoding ZNF216 or AWP1 becomes the marker for diagnosis of the disuse muscular atrophy.

Furthermore, the present invention provides a method for evaluating the risk of onset of the disuse muscular atrophy, which uses ZNF216 or AWP1 or the gene encoding this protein, as with the case of utilizing the above-described interaction between the proteasome and ZNF216 or AWP1.

The risk of onset of the disuse muscular atrophy when an individual would become bedridden in the future can be evaluated by examining the expression of ZNF216 or AWP1 found to be involved in the disuse muscular atrophy via the proteasome and examining the mutation or the single nucleotide polymorphism in the gene encoding this protein.

ZNF216 and AWP1 in the present invention are not limited narrowly to the proteins themselves having the amino acid sequences represented by SEQ ID No. 1 and No. 2, and include the proteins which interact with the proteasome or the polyubiquitin chain and have the amino acid sequence having one or more amino acid deletions, substitutions, additions or insertions in the above amino acid sequence. The base sequences of cDNA encoding ZNF216 and AWP1 in the present invention are shown in SEQ ID No. 3 and No. 4. For these base sequences, the present invention includes the base sequences having one or more base deletions, substitutions, additions or insertions in the above base sequence as long as the above interaction is not lost, and is not limited narrowly to the encoding proteins themselves.

As in the above, it has been revealed that the proteasome known as the protein involved in the disuse muscular atrophy interacts with ZNF216 (or AWP1). Consequently, the present invention has a technical significance that this interaction as well as ZNF216 (or AWP1) or the gene encoding the protein serve for drug discovery technology, diagnostic technology, examination technology, evaluation technology of the risk of onset of the disuse muscular atrophy, etc. Also it has been revealed that the polyubiquitin chain involved in the proteolytic system of proteasome interacts with ZNF216 (or AWP1). As a result, the present invention has the technical significance that this interaction as well as ZNF216 (or AWP1) or the gene encoding the protein particularly serve for drug discovery technology, diagnostic technology, examination technology, evaluation technology of the risk of onset of the disuse muscular atrophy, etc.

According to the present invention, it has been revealed that the proteasome interacts with ZNF216 (or AWP1). Also, it has been revealed that the polyubiquitin chain interacts with ZNF216 (or AWP1). By utilizing these newly found findings for the interaction between the proteins, it is possible to provide the therapeutic agent for the disuse muscular atrophy. The novel interaction revealed in the present invention is particularly useful for drug discovery, diagnosis, examination, evaluation of the onset risk for the disuse muscular atrophy, etc.

EXAMPLE 1

The present inventors efficiently searched a "partner protein" which recognizes ZNF216 (protein having the amino acid sequence represented by SEQ ID No. 1) and AWP1 (protein having the amino acid sequence represented by SEQ ID No. 2) and interacts therewith by the following method.

For ZNF216 (and AWP1), cDNA encoding this protein was prepared by RT-PCR method. And the cDNA encoding ZNF216 (or AWP1) was incorporated in pcDNA-FLAG (plasmid) using restriction enzymes to produce an expression vector. The present inventors have obtained pcDNA-FLAG by uniquely modifying based on pcDNA3 (plasmid, Invitrogen Corporation.) so that a FLAG recognition sequence is sequenced following a methionine residue for translation initiation at an N terminal side when ZNF216 (or AWP1) is expressed. When the cDNA encoding ZNF216 (or AWP1) is incorporated in pcDNA-FLAG, the cDNA encoding ZNF216 (or AWP1), in which the sequence encoding the methionine for the translation initiation is deleted by cleaving the methionine for the translation initiation of ZNF216 (or AWP1) with restriction enzymes, was introduced into pcDNA-FLAG (plasmid). The "FLAG recognition sequence" refers to the amino acid sequence "DYKDDDDK", and works as a tag (label) for the FLAG recognition sequence to recognize the objective protein by previously incorporating this amino acid sequence into a terminal sequence of the objective protein (ZNF216 or AWP1 in this experiment).

Subsequently, cultured cells were transfected with the expression vector (recombinant pcDNA-FLAG) in which the ZNF216 gene (or AWP1 gene) is incorporated and the FLAG recognition sequence is attached (transfection). HEK293T cells were used as the cultured cells to be transfected, and PolyFect supplied from Qiagen was used as a transfection reagent. The gene was transfected by the procedures according to the protocol of the same product.

A recombinant protein fused with the tag is expressed in the transfected cultured cells. The expressed partial recombinant ZNF216 (or AWP1) interacts with an unknown partner protein present in the cells to form a complex. The complex of ZNF216 (or AWP1) with the unknown partner protein was extracted from the cells by publicly known "immunoprecipitation method" using an antibody against the tag attached to ZNF216 (or AWP1).

An extraction method is as follows. The cells transfected with the gene were solubilized using a solubilization buffer (20 mM HEPES, pH 7.5, 150 mM NaCl, 50 mM NaF, 1 mM $Na_3VO_4$, 1 mM PMSF, 1% Triton X100). After adding this solubilization buffer, the cells were scraped to collect in a centrifuging tube, which was then subjected to ultracentrifugation (55,000 rpm, 4° C., 20 minutes).

Agarose beads to which a FLAG peptide antibody immobilized (purchased from Sigma) were added to a cell extract solution (supernatant) after the centrifugation, and stirred at 4° C. for 3 hours. The beads after stirring were collected by the centrifugation (1,000 rpm, 4° C., one minute), washed with the solubilization buffer, and ZNF216 (or AWP1) bound to the beads was eluted by adding the buffer containing the FLAG peptide to collect the protein complex in which the objective partner protein had been bound to ZNF216 (or AWP1).

After collecting the protein complex, the partner protein of the interaction was identified by the publicly known method referred to as a "mass tag method" using a publicly known tandem mass spectrometer (MS/MS) ("Analytical Methods of Proteome" edited by Toshiaki Isobe and Nobuhiro Takahashi, pp 129-142, Yodosha). A specific procedure is as follows.

First, a collected sample was centrifuged and concentrated, and then dissolved in a buffer for an enzymatic reaction (100 mM Tris, pH 8.8). Subsequently, the sample was digested with "trypsin" or "lysyl endopeptidase" which was an enzyme to recognize and cleave a particular amino acid. Lysyl endopeptidase was used in this experiment. Lysyl endopeptidase was added so that an enzyme substrate ratio (weight ratio) was 1/100 to 1/50, and reacted at 37° C. for 12 hours to yield a digested product. And the digested product was measured by the tandem mass spectrometer to obtain a mass value and internal amino acid sequence information of each digested peptide.

Using the mass values of peptide fragments digested with the enzyme, a candidate amino acid sequence was selected by automatic search from the database, and a mass value set when the sequence was fragmented at each amino acid was calculated.

As the above database, "SwissProt" (Internet address:

ftp.ebi.ac.uk/pub/databases/sp_tr_nrdb/fasta/sprot.fas.Z) which is the protein database already published and "NCBI RefSeq" (Internet address:

ftp.ncbi.nih.gov/refseq/H_sapiens/mRNA_Prot/hs.faa.gz) which is the nucleic acid database were used.

The partner proteins of ZNF216 and AWP1 were identified by comparing this calculated value with a fragment ion actually measured (MS/MS spectrum), and consequently, it was found that both partner proteins corresponded to a protein group which composes the "proteasome". This has demonstrated that ZNF216 or AWP1 interacts with proteasome. The "polyubiquitin chain" was also identified as the partner protein of ZNF216 and AWP1. This has also demonstrated that ZNF216 or AWP1 interacts with the polyubiquitin chain.

EXAMPLE 2

In Example 2, the experiment was performed to identify that the polyubiquitin chain interacts with ZNF216 or AWP1 using GST (glutathione-S-transferase).

A fusion protein of ZNF216 and GST was produced in *Escherichia coli* by gene engineering technology. And the fusion protein was purified using a glutathione column (glutathione sepharose beads). Since GST is specifically bound to glutathione in the column, only ZNF216 fused with GST is trapped in the column. The trapped fusion protein was collected using an elution buffer.

Subsequently, the collected fusion protein of ZNF216 and GST was mixed with the polyubiquitin chain, the mixed solution was purified again using the glutathione column, and collected using the elution buffer.

In a collected solution, the polyubiquitin chain along with ZNF216 fused with GST was collected. This indicates that ZNF216 and the polyubiquitin chain have a binding affinity and interact with each other.

A fusion protein of AWP1 and GST was also produced by the same way as in the above, and the experiment to identify the interaction was performed likewise. As a result, it has been shown that the AWP1 and the polyubiquitin chain have the binding affinity and interact with each other as in the case with ZNF216.

EXAMPLE 3

Example 3 is the experiment which shows that ZNF216 is associated with muscular atrophy.

Muscular atrophy model mice produced by removing the sciatic nerve in mice and starvation-induced muscular atrophy model mice in which muscular atrophy had been caused by starving mice were prepared. And, the mRNA amount of the gene encoding ZNF216 and the expression amount of the ZNF216 protein in skeletal muscle tissue in these mice with muscular atrophy were measured. As a result, the mRNA amount of the gene encoding ZNF216 and the expression amount of the ZNF216 protein were remarkably increased in the mice with muscular atrophy. This indicates that ZNF216 is involved in the mechanism in which muscular atrophy is caused.

EXAMPLE 4

In Example 4, by practically applying the RNA interference, the experiment in which the expression of AWP1 (protein having the amino acid sequence represented by SEQ ID No. 2) was inhibited using double strand RNA having the base sequence represented by SEQ ID No. 5 was performed.

In this experiment, (1) the sequence represented by SEQ ID No. 5 was designed to synthesize DNA, (2) the DNA corresponding to SEQ ID No. 5 was incorporated into a plasmid vector using restriction enzymes and a ligation reaction, (3) a viral vector (retrovirus) was made from the plasmid vector by transfection, (4) target cells (cultured murine cells) were infected with the recombinant virus, and (5) the effect of RNA interference was determined (see "RNAi Jikken Protocol" edited by Kazunari Taira et al., pp 116-128, Yodosha). The specific procedure is as follows.

The sequence of SEQ ID No. 5 is designed as follows. The First "GGATCC" sequence is cleaved by the restriction enzyme (BamH1 in this design) when introduced into the plasmid vector. The subsequent "ATGGCATGTGTTCAGTATG" sequence (19 bases) is a sense chain and the sequence corresponding to a part of the base sequence encoding AWP1. The subsequent "TTCAAGAGA" sequence is a linker sequence and is designed in order to curve in a hairpin shape to form a stem-loop structure when the sense chain and an antisense chain described later form a double strand. The subsequent "CATACTGAACACATGCCAT" sequence (19 bases) is the antisense chain and is complementary to the above sense chain. The subsequent "TTTTT" sequence is a terminator sequence (transcription termination part of mRNA). Subsequently, the portion from the H1 promoter sequence present in LTR (repeat sequence) at 3' terminus of the recombinant retrovirus to this terminator sequence is transcribed by RNA polymerase 3 to express the objective mRNA. The last "GTCGAC" sequence is also cleaved by the restriction enzyme (Sal1 in this design) when introduced into the plasmid vector. Subsequently, when the double strand RNA is formed, the sense chain and the antisense chain are complementarily bound to form the double strand, and the linker sequence curves in a hairpin shape to allow the sense chain and the antisense chain to be bound. As in the above, the sequence of SEQ ID No. 5 was designed and the DNA (oligonucleotide) having the sequence of SEQ ID No. 5 was synthesized.

Subsequently, in this experiment, the synthesized DNA was incorporated into the plasmid vector using the restriction enzymes and the ligation method. The plasmid vector was uniquely made by the present inventors, and the sequence encoding the recombinant retrovirus was incorporated therein in advance. The sequence encoding the recombinant retrovirus is identical to the cDNA sequence reversely transcribed from the retrovirus, but the genes required for the process from the viral infection to the incorporation into the DNA of the host cells are left, and the sequences involved in the expression of viral genome and viral proteins are eliminated. An expression unit of a drug (puromycin) resistant gene had been inserted in the sequence encoding this recombinant retrovirus, which was designed to select only cells infected with the virus by treating with puromycin. And in the sequence encoding this recombinant retrovirus, there are the H1 promoter sequence and the subsequent sequence cleaved with two restriction enzymes (Bgl1 and Sal1 in this design) in the 3' LTR sequence. Cleaved ends of the restriction enzyme Bgl2 are identical to those of Bgl1.

When the synthesized DNA was incorporated into the plasmid vector, the cleaved sites of synthesized DNA and cloning sites of the plasmid were cleaved with two restriction enzymes at two sites, respectively, and then the synthesized DNA and the plasmid vector were ligated using a ligation kit. In this experiment, the synthesized DNA was cleaved with BamH1 and Sal1, and the plasmid was cleaved with Bgl2 and Sal1. The cleaved ends of BamH1 and Bgl2 are identical. Thus, the synthesized DNA was incorporated into the plasmid by ligating the site of the synthesized DNA cleaved with BamH1 to the site of plasmid cleaved with Bgl2 and ligating the site of the synthesized DNA cleaved with sal1 to the site of the plasmid cleaved with Sal1. And, the plasmid vector in which the synthesized DNA had been incorporated was subcloned using competent cells, and subsequently the cloned recombinant plasmid vector was purified.

Subsequently, the recombinant retrovirus was produced by transfecting cultured cells with the recombinant plasmid vector purified by the above procedures. Here, the recombinant plasmid vector contains the sequence encoding the recombinant retrovirus, but the recombinant retrovirus is not produced because all genes required for completing the retrovirus and releasing it out of the cells have been previously eliminated from this sequence. Thus, when transfected, another plasmid in which the genes encoding the proteins required for completing the retrovirus had been incorporated in advance was simultaneously transfected to complete the retrovirus in the cultured cells and release it out of the cells. The recombinant retrovirus released out of the cells, in which the synthesized DNA had been incorporated, was collected.

And, the cultured murine cells were infected with the recombinant retrovirus. For this recombinant virus, cDNA is synthesized after the infection by being reversely transcribed, and the cDNA is incorporated into the DNA sequences of the host cells, but the retrovirus is not expressed because the sequence required for expressing the retrovirus has been eliminated in advance. And, in the sequence incorporated in the host cells, the portion from the H1 promoter sequence to the transcription termination sequence is transcribed by the action of RNA polymerase 3 present in the host cells. By the above procedures, the cultured murine cell in which the synthesized RNA was stably expressed was made. This synthesized RNA undergoes modifications such as removal of the linker sequence in the host cells to become the double strand RNA which causes the RNA interference. By the presence of this double strand RNA in the cultured murine cell, corresponding mRNA is specifically decomposed to inhibit the expression of the corresponding protein.

It was determined by a Northern blotting method for mRNA encoding AWP1 whether the RNA interference had been caused by the double strand RNA. RNA was extracted from the cultured murine cells infected with the recombinant retrovirus, and the expression amount of mRNA encoding AWP1 was examined. As a result, it was found that the expression of AWP1 was inhibited.

From the above result, it has been found that the expression of AWP1 can be inhibited by practically applying the RNA interference. By inhibiting the expression of AWP1, the interaction between AWP1 and the proteasome or the interaction between AWP1 and the polyubiquitin chain is also inhibited. By inhibiting these interactions, the decomposition of the muscle-composing protein by the proteasome does not occur even in the case of the disuse muscular atrophy, etc., which occurs in the state such as prolonged bed rest such as being bedridden, neuroparalysis, prolonged fixation of four limbs and prolonged stay in a space environment, where weight load to muscle is remarkably reduced because signals are not transmitted to the proteasome. Therefore, the double strand RNA which practically applies the RNA interference is effective as the therapeutic agent for the disuse muscular atrophy.

This Example is only one of the Examples which indicate that the double strand RNA which practically applies the RNA interference is effective as the therapeutic agent for the disuse muscular atrophy, and the present invention is not limited narrowly to this Example. In particular, the method and the means of the experiment and the selection of the sequence of the double strand RNA used for the RNA interference are not narrowly limited.

What is claimed is:

1. A method for screening therapeutic agents for disuse muscular atrophy comprising the step of interacting a protein composed of SEQ ID No. 1 with a polyubiquitin chain.

2. The method defined in claim 1, further comprising the steps of carrying out said interaction step in the presence of a candidate therapeutic agent, and determining the affect of the candidate therapeutic agent on a binding strength between the protein composed of SEQ ID No. 1 and the polyubiquitin chain.

3. The method defined in claim 2, wherein said steps are carried out by way of an enzyme-linked immunosorbent assay, and said affect on said binding strength is determined by color development on a substrate.

4. The method defined in claim 2, wherein said affect on binding strength is determined by direct observation of at least one molecule of the combination of the SEQ ID No. 1 and the polyubiquitin chain.

5. The method defined in claim 4, wherein said direct observation is conducted by one of NMR spectroscopy, X-ray crystal analysis, electron microscopy and surface plasmon resonance.

* * * * *